United States Patent [19]

Jensen

[11] Patent Number: 4,971,830
[45] Date of Patent: Nov. 20, 1990

[54] METHOD OF ELECTRODE FABRICATION FOR SOLID OXIDE ELECTROCHEMICAL CELLS

[75] Inventor: Russell R. Jensen, Murrysville, Pa.

[73] Assignee: Westinghouse Electric Corp., Pittsburgh, Pa.

[21] Appl. No.: 473,528

[22] Filed: Feb. 1, 1990

[51] Int. Cl.$^5$ .............................................. B05D 1/00
[52] U.S. Cl. ...................... 427/34; 427/115;
427/123; 427/125; 427/126.3; 427/201;
427/203; 427/205; 427/377; 427/383.3;
427/423
[58] Field of Search .................. 427/34, 245, 383.1,
427/115, 123, 125, 126.3, 201, 205, 377, 383.3,
423

[56] References Cited

U.S. PATENT DOCUMENTS 4,490,444 12/1984 Isenberg .................................. 429/31
4,582,766 4/1986 Isenberg et al. ....................... 429/30
4,597,170 7/1986 Isenberg ............................. 29/623.5

Primary Examiner—Bernard Pianalto
Attorney, Agent, or Firm—A. Mich, Jr.

[57] ABSTRACT

A process for fabricating cermet electrodes for solid oxide electrochemical cells by sintering is disclosed. First, a porous metal electrode is fabricated on a solid oxide cell, such as a fuel cell by, for example, sintering, and is then infiltrated with a high volume fraction stabilized zirconia suspension. A second sintering step is used to sinter the infiltrated zirconia to a high density in order to more securely attach the electrode to the solid oxide electrolyte of the cell. High performance fuel electrodes can be obtained with this process. Further electrode performance enhancement may be achieved if stabilized zirconia doped with cerium oxide, chromium oxide, titanium oxide, and/or praseodymium oxide for electronic conduction is used.

12 Claims, 4 Drawing Sheets

METHOD OF ELECTRODE FABRICATION FOR SOLID OXIDE ELECTROCHEMICAL CELLS

GOVERNMENT CONTRACT

The Government of the United States of America has rights in this invention pursuant to Contract No. DEAC-0280-ET-17089 awarded by the U.S. Department of Energy.

BACKGROUND OF THE INVENTION

1. Field of the Invention

The present invention relates to electrodes for solid oxide electrochemical cells and more specifically to a method of fabricating electrodes on solid oxide electrochemical cells by sintering. In this case, electrochemical cells include fuel cells, electrolyzers and sensors that operate on the basis of electromotive force measurement and/or current measurement and which comprise a solid oxide electrolyte and attached electrodes. Solid oxide fuel cells are one typical field of application of this invention. Although this invention was developed specifically for the fabrication of electrodes on fuel cells, it may also be used to fabricate electrodes on a variety of other electrochemical devices.

2. Description of the Prior Art

Solid oxide fuel cells are high temperature electrochemical devices fabricated primarily from oxide ceramics. Typically, they contain an oxygen ion conducting solid electrolyte, such as stabilized zirconia. The electrolyte is usually a thin dense film which separates two porous electrodes—an anode and a cathode. The cathode, which is maintained in an oxidizing atmosphere, is usually an oxide doped for high electrical conductivity, such as strontium doped lanthanum manganite. The anode, on the other hand, is maintained in a reducing atmosphere and is usually a cermet such as nickel-zirconia. Finally, an interconnection is usually employed which is a dense, electronically conducting oxide material which is stable in both reducing and oxidizing environments, such as doped lanthanum chromite. The interconnection is deposited on a cell as a thin gas tight layer in such a manner that it permits the anodes and cathodes of adjacent cells to be electrically connected in series. The gas-tightness of the interconnection, in combination with that of the electrolyte, insures that the entire cell is gas-tight, preventing mixing of the anode and cathode atmospheres.

Solid oxide cells can be operated in either an electrolysis mode or in a fuel cell mode. In an electrolysis mode, DC electrical power and steam or carbon dioxide or mixtures thereof are supplied to the cell which then decomposes the gas to form hydrogen or carbon monoxide or mixtures thereof, as well as oxygen. In the fuel cell mode, the cell operates by electrochemically oxidizing a gaseous fuel such as hydrogen, carbon monoxide, methane or other fuels to produce electricity and heat.

The use of nickel-zirconia cermet anodes for solid oxide electrolyte fuel cells is well known in the art, and taught, for example, by A. O. Isenberg in U.S. Pat. No. 4,490,444. The anode must be compatible in chemical, electrical, and physical-mechanical characteristics such as thermal expansion, to the solid oxide electrolyte to which it is attached. A. O. Isenberg, in U.S. Pat. No. 4,597,170 solved bonding and thermal expansion problems between the anode and solid oxide electrolyte, by use of a skeletal embedding growth, of for example, primarily ionically conducting zirconia doped with minor amounts of yttria. The skeletal growth extends from the electrolyte/anode interface into a porous nickel layer, with the composite structure comprising the porous cermet anode.

Anchoring of the porous nickel anode to the solid oxide electrolyte was accomplished by a modified electrochemical vapor deposition (EVD) process. While this process provided well bonded anodes, having good mechanical strength and thermal expansion compatibility, gas diffusion overvoltages were observed during operation, lowering overall cell performance.

In order to reduce gas diffusion overvoltages, A. O. Isenberg et al., in U.S. Pat. No. 4,582,766, taught oxidizing the nickel in the cermet electrode to form a metal oxide layer between the metal, and the electrolyte, the embedding skeletal member. Subsequent reduction of the metal oxide layer forms a porous metal layer between the metal, and the electrolyte and skeletal member allowing greater electrochemical activity. The EVD process, while producing acceptable quality electrodes is labor-intensive. What is needed is a low cost process for the fabrication of active anode structures in order to eliminate the need for electrochemical vapor deposition.

SUMMARY OF THE INVENTION

The above problems have been solved and the above needs have been met by providing a process for sintering anodes on solid oxide fuel cells (SOFC). As mentioned above, this process could also be used to fabricate electrodes on other types of electrochemical devices.

For reasons of cost reduction while maintaining cell performance and structural stability, an alternative to EVD has been developed for fuel cell anode fabrication. A sintering process has been devised which is significantly less expensive than EVD. In addition, the microstructure of the sintered anode is more amenable to modification and control, allowing the performance of a cell to be optimized.

Specifically, a porous metal electrode is applied onto a fuel cell and subsequently infiltrated with a high volume fraction yttria stabilized zirconia suspension. A sintering operation may then be used to sinter the stabilized zirconia to full density, thereby attaching the electrode to the cell. The porous metal electrode has been fabricated by preferably sintering the metal layer onto the electrolyte of a cell. Other methods of applying the porous nickel layer, such as plasma or flame spraying may also be used.

It is an object of the present invention to provide a method of fabricating a cermet solid oxide electrochemical cell electrode by sintering.

It is an object of the present invention to provide a method of making a cermet electrode by applying a porous metallic electrode material to the electrolyte of a solid oxide electrochemical cell then infiltrating the metallic electrode material with a high volume fraction suspension of stabilized zirconia and sintering this structure onto the cell.

It is a further object of the present invention to provide an electrochemically active anode for solid oxide fuel cells.

It is yet another object of the present invention to provide an economical method of producing a solid oxide electrochemical cell electrode.

It is an object of the present invention to provide a structurally stable solid oxide electrochemical cell electrode.

It is a further object of the present invention to provide a method for the fabrication of cermet electrodes for solid oxide electrochemical cells in which the metallic component comprises one or more of the metals of Group VIII of the Periodic Table of Elements, individually or as alloys, and in which the ceramic component is stabilized zirconia.

These and other objects of the present invention will be more fully understood from the following description of the invention.

BRIEF DESCRIPTION OF THE DRAWINGS

FIG. 1 is a plot of slip viscosity.

FIG. 4 is fuel cell performance test data.

DETAILED DESCRIPTION OF THE PREFERRED EMBODIMENTS

Figure 1:
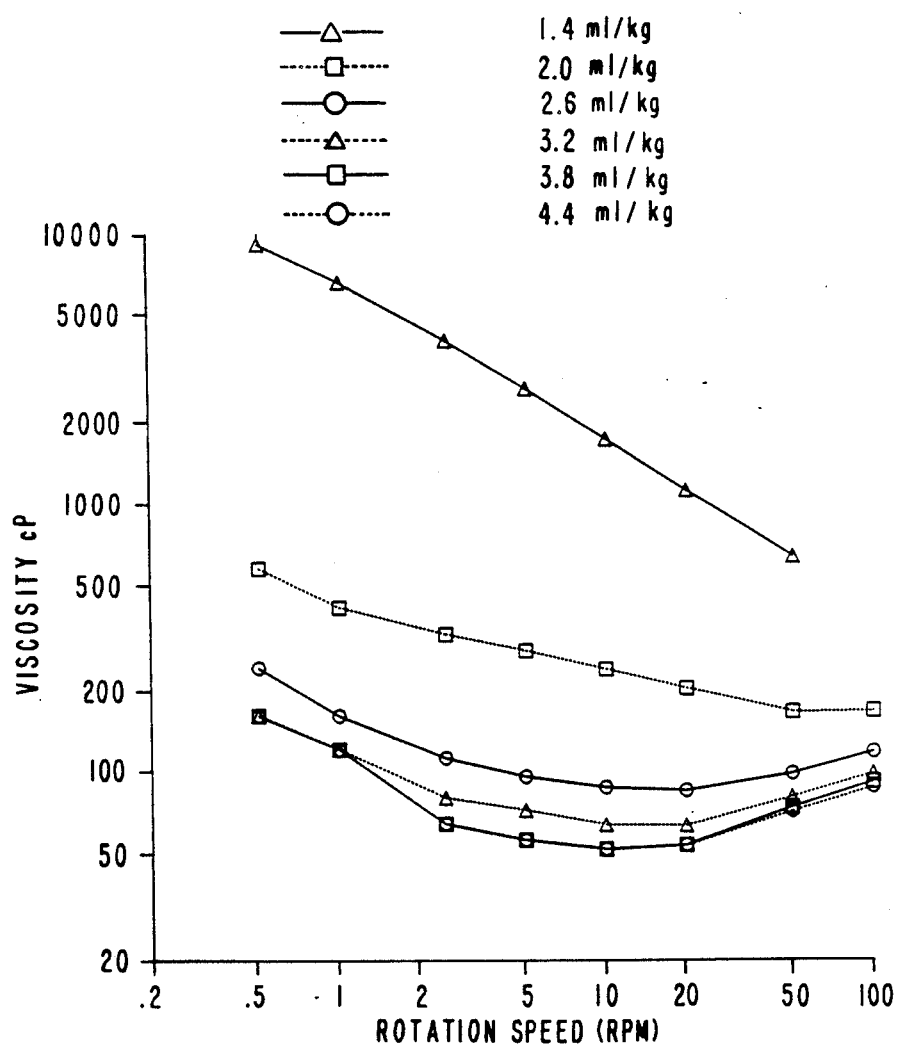
FIG. 1 is a plot showing the behavior of the viscosity of a 30 volume percent (72 weight percent) aqueous suspension of yttria stabilized zirconia during dispersing of the zirconia with 4 molar nitric acid.

For purposes of convenience, references to zirconia and to yttria stabilized zirconia mean stabilized zirconia in which the stabilizing agent is a divalent or trivalent cation species such as calcium, magnesium, yttrium or other such species. The metallic component of the electrode is preferably nickel, however, any metal with a melting point in excess of the temperature used in sintering the infiltrated zirconia may be used. Suitable metals include metals from Group VIII of the Periodic Table of Elements, such as palladium, platinum, cobalt and the like. Nickel shall be used throughout the specification in order to simplify description but the invention is not limited to nickel.

The anode of a solid oxide fuel cell performs two main functions. First, it acts as an electron current collector (or distributor of electrons if the fuel cell is operated in the electrolysis mode). The electrode must collect the electrons liberated during the electrochemical oxidation of the fuel and provide a low resistance path for electron current flow to either a series connected fuel cell or an external power lead. To obtain the lowest electrode resistance and maximum power from a fuel cell, the current collector within an anode should be metallic.

The second important function of the anode is to provide sites where the electrochemical oxidation (or reduction if the fuel cell is operated in the electrolysis mode) of the fuel can occur. The microstructural requirements of such sites are stringent. They are locations within the anode where oxygen ions delivered by the electrolyte, gaseous fuel from the fuel stream and an electronic path to the electron current collector are simultaneously in contact.

The sintered anode of the present invention possesses numerous sites where open porosity (accessible by fuel from the fuel stream) is in contact with both the sintered yttria stabilized zirconia and nickel. Because the yttria stabilized zirconia in the anode is in contact with the electrolyte and the nickel is electrically conducting, these three phase sites are electrochemically active. Thus, anode fabrication by sintering mixtures of yttria stabilized zirconia and nickel provides a method for the fabrication of fuel cells with performance at least comparable to that of prior art fuel cells.

The infiltrate/sinter fuel electrode sintering process of the present invention provides two steps. First, a porous nickel layer is applied to the electrolyte of a cell. This may be done by first applying a nickel powder slurry containing a binder and a small amount of zirconia to control shrinkage during sintering to the cell and then sintering the coated cell at a relatively low temperature. After this presintering operation, the nickel layer is consolidated and is electrically conductive, but is not well attached to the electrolyte of the cell. Porous nickel layers may also be applied by other methods, such as plasma or flame spraying. The porous nickel layer is then infiltrated with a low viscosity, high volume fraction aqueous zirconia suspension with an optimal additive of a suitable dispersant. When the electrode is dried, the zirconia is deposited as a green body in the porosity of the presintered nickel layer, extending from the electrode/electrolyte interface to the outer surface of the electrode. Adequate dispersion of the zirconia suspension gives the zirconia a relatively high green density and allows a relatively low zirconia sintering temperature. Following a zirconia sintering operation, the densified zirconia at the electrode/electrolyte interface serves to attach the electrode to the cell. The remainder of the zirconia in the electrode provides sintering resistance during long term operation. The overall microstructure is somewhat similar to that obtained by EVD anode fabrication.

In addition to being a potentially low-cost process, the ability to fabricate anodes by sintering presents an important advantage in that the composition and structure of the anode may be tailored to a greater degree than is possible in fabrication by EVD. For instance, the zirconia infiltrated into the electrode does not necessarily have to be a purely ionically conducting stabilized zirconia, but could be some suitably doped mixed electronically-ionically conducting stabilized zirconia. The use of mixed conductor zirconia in the anode increases fuel cell performance because the mixed conducting zirconia can then perform two functions, the delivery of the oxygen ions conducted through the electrolyte and conduction of electrons liberated in the electrochemical oxidation of the fuel to the current collector. This greatly reduces the geometrical constraints on the electrochemically active sites in the fuel electrode. In effect, the entire surface of the mixed conductor zirconia in contact with the fuel atmosphere becomes electrochemically active. Stabilized zirconia powders may be doped to give mixed ionic and electronic conductivity. Suitable dopants include cerium oxide, titanium oxide, chromium oxide or praseodymium oxide mixtures thereof and the like.

EXAMPLES

The infiltrate/sinter process for fabricating fuel cell anodes as practiced comprises five main steps. These are
- formulation of a nickel metal powder slurry, application and presintering of the nickel slurry onto a cell, formulation of a yttria stabilized zirconia suspension, infiltration of the presintered nickel with the zirconia suspension and resintering of the cell to densify the infiltrated zirconia. The nickel slurry formulation, application and presintering steps are applicable to fabrication of the porous nickel electrode layer by sintering. These steps would be altered if alternate methods of applying this layer were to be used. In particular, it should be feasible to apply the porous nickel layer to a fuel cell without using a presintering operation, thereby simplifying the process to include only one high temperature sintering operation to densify the infiltrated zirconia. The five steps as practiced are addressed below.

Nickel Slurry Formulation

The essential components of the nickel slurry are nickel metal powder, an organic binder and a small amount of yttria stabilized zirconia to control shrinkage during sintering. The slurry may be based on either an aqueous or organic medium. An aqueous slurry is preferred on the basis of safety considerations.

The nickel metal powder that is preferred for the slurry has a chain-like or filamentary morphology. Individual powder particles comprise smaller, roughly equiaxed particles attached to form a chain-like structure resembling beads on a string. A commercial example of this type powder is INCO Type 287 nickel powder. This type nickel powder is preferred over other more equiaxed nickel powders, such as INCO Type 123 nickel powder, because the structure inherent in these powder particles leads to a higher porosity in the slurry applied layers after sintering. High porosity is desirable because it allows the maximum amount of zirconia to be deposited from a suspension in the sintered nickel layer.

The binder is added to the nickel slurry to consolidate the coating after the suspension medium is eliminated by evaporation. A medium molecular weight, fully hydrolyzed grade of polyvinyl alcohol-Dupont Elvanol Grade 75-15 has been used. Other types of binders might be expected to work equally as well.

It has been found that a small addition of a fine yttria stabilized zirconia powder to the slurry is beneficial in controlling the shrinkage which occurs when the nickel slurry coating is sintered. This addition helps prevent excessive shrinkage of the coating and peeling of the coating from the surface of the fuel cell. The powder that has been used is TZ-8Y yttria stabilized zirconia powder from TOSOH.

TABLE 1

| Nickel Slurry Formulation | |
|---|---|
| Component | Composition* |
| Nickel Powder+ | 50% to 60% |
| Binder Solution++ | 40% to 50% |
| Zirconia Powder+++ | Added after mixing of nickel powder and binder solution at the rate of 0.5 to 5.0 weight percent of the nickel powder weight in the slurry. |

*Weight basis.
+INCO Type 287 nickel powder.
++Aqueous solution of 6 weight percent DuPont Elvanol 75-15.
+++TOSOH TZ-8Y yttria stabilized zirconia powder.

A typical nickel slurry formulation is given in Table 1. The nickel powder is first added to the aqueous binder solution. The binder solution has been used at a 6 weight percent formulation. Other formulations in a range of about 3 to 12 weight percent can be used. The ratio of nickel powder to binder solution can be varied to adjust the viscosity of the slurry for proper applied thickness. After mixing of the nickel powder and the binder solution zirconia powder is added to the slurry. TOSOH TZ-8Y yttria stabilized zirconia has been used. Other types of zirconia powder may also be used, with the amount of the addition modified by the particle size of the powder; proportionally greater amounts of powder are required the greater the particle size of the powder. The powder used is added at a rate that lies in the range of 0.5% to 5.0% of the weight of nickel powder in the slurry. The optimum addition of zirconia powder to the slurry is governed by the sintering conditions. Greater amounts of zirconia are required if the sintering time and temperature are increased.

Nickel Slurry Application and Sintering

The nickel slurry is applied to a fuel cell by dipping the cell in the slurry and allowing excess slurry to drip off the cell as the coating dries. Areas of the cell which are not to be coated are masked with tape, which is removed immediately following application of the slurry. The coating is applied to a thickness in the range of 50 $\mu$m to 250 $\mu$m.

After the slurry applied coating is dried, the cell is sintered to consolidate the nickel particles in the coating into a porous layer. The sintering temperature can be in the range of about 800° C. to 1100° C. for times ranging from 1 hour to 20 hours. The amount of zirconia powder added to the slurry is governed by the actual sintering conditions used. Greater amounts of zirconia are required to control the sintering of the nickel layer, the higher the sintering temperature or the longer the sintering time. For example, a 5 weight percent addition of zirconia to the slurry (relative to the weight of the nickel in the slurry) was used for sintering conditions of 1100° C. for 16 hours. For sintering the nickel layer at 1000° C. for 2 hours, a zirconia addition of 1 weight percent was used.

The sintering atmosphere that is preferred is ambient temperature humidified nitrogen. The composition of this gas is approximately 98% $N_2$ and 2% $H_2O$. This composition is preferred over, say a nitrogen-hydrogen mixture, because it allows the nickel particle layer to sinter with little or no shrinkage. Shrinkage is undesirable because it causes the porous nickel layer to shift on the surface of the cell and can lead to lifting and peeling of the layer from the cell. The zirconia powder addition to the slurry material also helps control sintering induced shrinkage. This addition by itself is, however, not completely effective in controlling shrinkage. For example, in a nitrogen-hydrogen atmosphere, zirconia powder containing nickel layers may still shrink and peel. It is believed that the humidified nitrogen atmosphere is effective in sintering the nickel layer because it causes the formation of a thin layer of nickel oxide on the surfaces of the nickel particles. At the temperatures used, nickel oxide is volatile in the sintering atmosphere as a hydroxide species. This can lead to sintering by vapor phase transport, which can occur with little or no shrinkage.

Following the hold at the sintering temperature, the cell with the sintered nickel layer is allowed to furnace cool. During this time, the atmosphere is made reducing by the addition of hydrogen to the humidified nitrogen, to give 3% to 5% $H_2$ in the sintering atmosphere. This change is made to ensure that any nickel oxide formed during the hold at the sintering temperature is reduced to metallic nickel.

Following sintering, the nickel powder slurry coating is consolidated into a porous nickel layer which is electrically conducting. The porosity of the layer is in the range of 70% to 80% when the preferred filamentary nickel powder is used. In itself, the porous nickel layer would behave as a fuel cell anode except that it exhibits little adhesion to the electrolyte of the fuel cell. To adhere the nickel layer to the cell, the electrode is infiltrated with zirconia and sintered to densify the zirconia.

Zirconia Suspension

The essential novelty of this invention is the recognition that a high volume fraction, low viscosity zirconia suspension will infiltrate a sufficiently porous body as if it was a single phase fluid. When dried, the infiltrated suspension deposits significant amounts of zirconia intimately throughout the porosity of the body, which can subsequently be densified by sintering.

The most critical aspect of formulating the zirconia suspension is to achieve as low a viscosity as possible at zirconia contents in the range of about 20 to 30 volume percent. As discussed below, the preferred suspension composition lies within this range. For 8 mole percent yttria stabilized zirconia, this range corresponds to zirconia contents in the range of about 60 to 72 weight percent. Another important aspect of the suspension is that the zirconia powder should have an extremely small average particle size so that it has a high sinterability. The specific surface area of the zirconia powder should be above 20 m$^2$/g; such powder can be obtained commercially (TOSOH, TZ-8Y 8 mole percent yttria stabilized zirconia).

As mentioned, it is desirable to formulate an aqueous zirconia suspension on the basis of safety considerations. An aqueous suspension is also preferred because water is less volatile than many of the commonly used organic media. This is important when a presintered nickel anode is to be infiltrated with zirconia, as discussed below. The only other component of the suspension is a dispersant to deflocculate the zirconia.

Any method of dispersing the zirconia powder in the suspension can be used as long as a low viscosity, approximately Newtonian suspension is obtained. Commonly used methods include pH adjustment and addition of an organic dispersant, either a polyelectrolyte or neutral polymer. A method that has worked well with the zirconia powder used is acidic pH adjustment with nitric acid. FIG. 1 shows the viscosity behavior of a 30 volume percent zirconia suspension with successive additions of a 4 molar nitric acid solution. As shown, successive additions of the acid reduce the viscosity of the suspension and lead to approximately Newtonian behavior, where viscosity is independent of shear rate. No further acid additions are made when a previous addition caused little or no change in viscosity behavior, as shown in the figure. The viscosity curves shown in FIG. 1 should be regarded as only semiquantitative as they were obtained with a spindle type viscometer under non-standard conditions. Despite the relatively high zirconia content of 30 volume percent, the viscosity of the suspension is less than or approximately equal to 100 cP. After a light milling of several hours, the suspension is ready for use. An extremely stable suspension is obtained, with a shelf life of over one year (when the cake formed by slow sedimentation on the bottom of the suspension container is redispersed).

Zirconia Infiltration

After the nickel slurry applied coating is presintered to form a porous nickel layer on the electrolyte of a fuel cell, it is ready to be infiltrated with zirconia. Any area of the cell that is not covered by the nickel layer and on which zirconia deposition is undesirable can be masked with a suitable masking material which is not soluble in the suspension medium. For aqueous suspensions, petroleum jelly works well. The zirconia suspension drains from the masked area, leaving essentially no zirconia on the area when the suspension is dry.

The zirconia content of the zirconia suspension should be in the range of 20 to 30 volume percent. A suspension with a lower zirconia content does not deposit sufficient zirconia in the presintered nickel layer to attach the layer to the cell after the zirconia is sintered. A suspension with a higher zirconia content has a viscosity which is too high to allow complete infiltration of the nickel layer.

The presintered nickel layer can be infiltrated with the zirconia suspension simply by immersing the cell with the layer into the suspension. When a suspension with a zirconia content approaching 30 volume percent is employed, it is useful to perform the infiltration under vacuum. This is done by placing the vessel containing the suspension and the cell under vacuum. The vacuum aids in removing trapped air pockets from the nickel layer, which are then filled with suspension on removal of vacuum from the vessel. Vacuum infiltration gives a slight increase in the amount of zirconia infiltrated into the nickel layer for the higher volume fraction suspensions than is obtained by ambient pressure infiltration of these suspensions. When vacuum infiltration is performed, aqueous suspensions are required because the vapor pressure of water at ambient temperature is low enough that a reasonably strong vacuum can be applied to the suspension without undue evaporation of the suspension medium. This is not the case with many of the commonly used organic media, which have relatively high vapor pressures and would evaporate during exposure to vacuum to an unacceptable degree.

Figure 2:
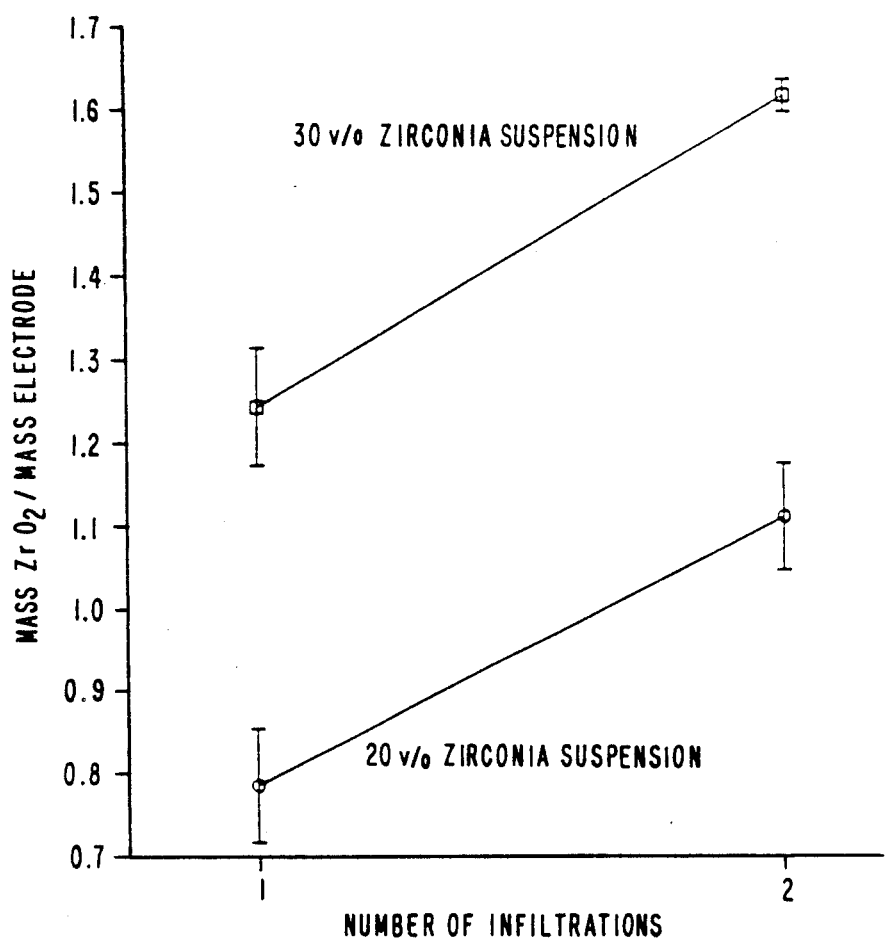
FIG. 2 is a plot of the effect of zirconia infiltration conditions on the relative amount of zirconia infiltrated into a presintered nickel anode.

FIG. 2 shows the dependence of the relative weight of zirconia infiltrated into the presintered nickel layer as a function of the infiltration conditions. All infiltrations shown were done under vacuum. The weight of infiltrated zirconia is given as the ratio of the weight of the zirconia to the weight of the presintered nickel layer. As expected, the amount of infiltrated zirconia increases with the zirconia volume fraction of the suspension. Reinfiltration of a porous nickel layer after the previously infiltrated zirconia suspension is allowed to dry is a viable technique for increasing the amount of infiltrated zirconia in the layer, as shown in FIG. 2.

There appears to be a minimum amount of zirconia which must be infiltrated into the porous nickel layer to obtain an adherent electrode following sintering of the zirconia. Of the four infiltration conditions shown in FIG. 2, the single infiltration of the 20 volume percent suspension resulted in a significantly less well bonded electrode after sintering to densify the zirconia. Accordingly, it is desirable to have the ratio of the weight of the infiltrated zirconia to the weight of the presintered porous nickel layer to be greater than or equal to about 1.0.

Zirconia Sintering

After the presintered nickel layer is infiltrated with zirconia, the cell can be resintered to densify the zirconia and attach the electrode to the cell. The temperature required to sinter the infiltrated zirconia is in the range of 1200° C. to 1350° C. This range applies to the type zirconia used in developing this process (TOSOH TZ-8Y). Lower specific surface area powder would require higher sintering temperatures. The hold time at the sintering temperature (sintering time) required to sinter the zirconia varies inversely with the sintering temperature. Sintering times of 8 hours and 30 minutes have been used for sintering temperatures of 1250° C. and 1300° C., respectively. The sintering atmosphere is kept reducing during the zirconia sintering operation. An atmosphere of dry nitrogen with 5% hydrogen has been used.

Microstructure and Performance

Figure 3A:
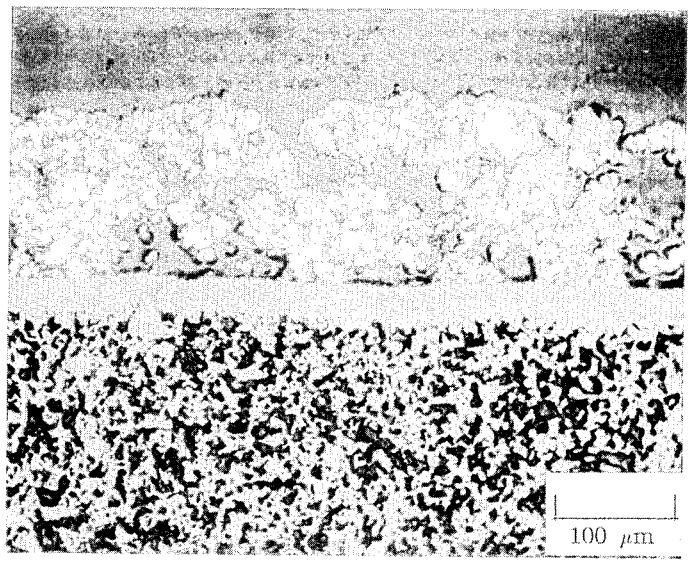
FIG. 3 is a photograph which illustrates the microstructure of an anode sintered on a cell by the present infiltrate/sinter method.
Figure 3B:
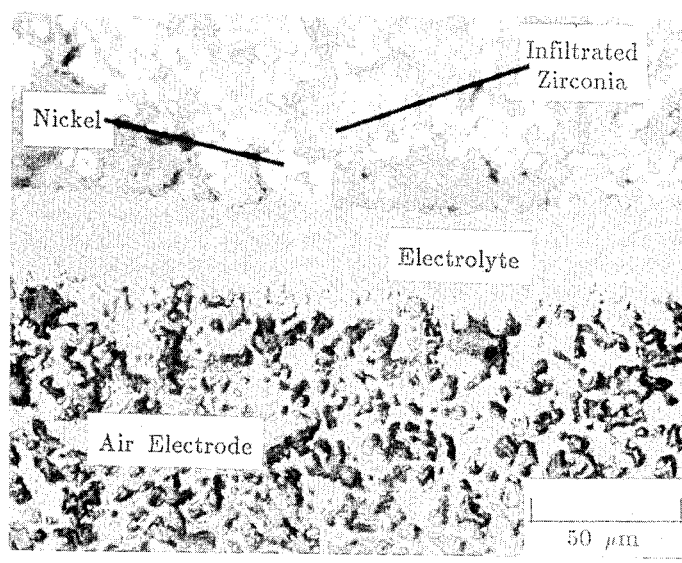

FIG. 3 shows the microstructure of an anode sintered on a cell using the present process. The electrode contains a large amount of densely sintered zirconia which prevents the nickel in the anode from sintering dense during cell operation. The zirconia extends from the outer surface of the anode to the anode/electrolyte interface. The zirconia at the base of the anode is well bonded to the electrolyte of the cell, giving the electrode good adhesion to the cell. The resulting electrode structure has numerous three phase contact points where porosity, zirconia and nickel are in contact, which are expected to be electrochemically active. Accordingly, the microstructure of the sintered anode is just that which should give good performance on a fuel cell.

Figure 4:
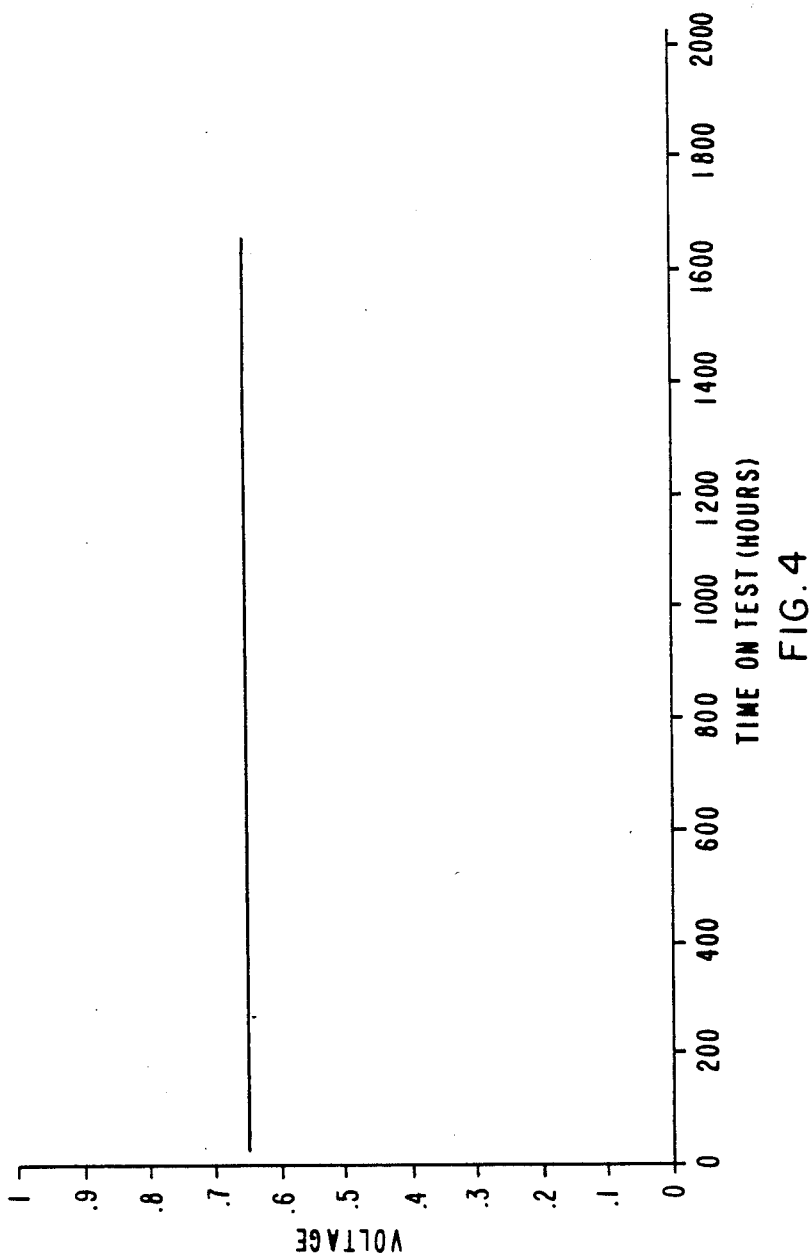
FIG. 4 is a plot showing the stability of the voltage output of a fuel cell with a sintered fuel electrode as a function of time during testing at 1000° C. and a current density of 250 mA/cm$^2$.

FIG. 4 shows the electrical performance of a fuel cell with a sintered anode when tested at 1000° C. and at a current density of 250 mA/cm$^2$. The resulting cell voltage was about 650 mV, which was stable for over 1500 hrs before termination of the test. This is excellent performance for the testing conditions used. This test demonstrates that the present sintering process, which is less expensive and simpler than the EVD process, is capable of producing cells with performance comparable to that of prior art cells.

Whereas particular embodiments of the invention have been described above for purposes of illustration, it will be appreciated by those skilled in the art that numerous variations of the details may be made without departing from the invention as described in the appended claims.

I claim:

1. A process for fabricating a metal-ceramic electrode structure for a solid oxide electrochemical cell comprising:
   (a) applying a layer of a porous metal onto a solid oxide electrolyte surface;
   (b) infiltrating said porous metal layer with a stabilized zirconia powder suspension;
   (c) sintering zirconia infiltrated porous metal layer to densify the zirconia 2. The process according to claim 1 including providing a metal selected from the group consisting of nickel, palladium, platinum and cobalt.

3. The process according to claim 1 including using zirconia powder stabilized with yttrium oxide, calcium oxide or magnesium oxide or mixtures thereof in step (b).

4. The process according to claim 1 including providing a zirconia suspension comprising about 20 to 30 v/o stabilized zirconia.

5. The process according to claim 1 including applying said porous metal layer in step (a) by sintering a metal powder layer onto the electrolyte of a cell.

6. The process according to claim 1 including applying a porous nickel layer in step (a) by sintering at a temperature in the range of 800° C. to 1100° C. and in a nitrogen-water vapor atmosphere.

7. The process according to claim 1 including flame spraying or plasma spraying said porous metal layer in step (a).

8. The process according to claim 1 including providing a dispersant in said zirconia suspension.

9. The process according to claim 1 including infiltrating said layer with said zirconia suspension at least once.

10. The process according to claim 1 including sintering said layer in step (c) at a temperature in the range of about 1200° C. to 1350° C. in a nitrogen-hydrogen or other reducing atmosphere.

11. The process according to claim 1 including using of stabilized zirconia powder doped for electronic conductivity.

12. The process according to claim 10 including using cerium oxide, chromium oxide, titanium oxide or praseodymium oxide and mixtures thereof as said dopants.

* * * * *